(12) United States Patent
Sim et al.

(10) Patent No.: US 8,541,035 B2
(45) Date of Patent: Sep. 24, 2013

(54) METHODS FOR PREPARING A FERMENTED GINSENG CONCENTRATE OR POWDER

(75) Inventors: Dae Keun Sim, Gyeonggi-do (KR); Jong Hwan Sung, Gyeonggi-do (KR); Seung Kwon Lee, Gyeonggi-do (KR); Min Goo Cho, Gyeonggi-do (KR)

(73) Assignee: Il Hwa Co., Ltd., Gyeonggi-do (KR)

( * ) Notice: Subject to any disclaimer, the term of this patent is extended or adjusted under 35 U.S.C. 154(b) by 52 days.

(21) Appl. No.: 12/466,093

(22) Filed: May 14, 2009

(65) Prior Publication Data

US 2010/0291244 A1 Nov. 18, 2010

(51) Int. Cl.
*A61K 36/26* (2006.01)
*A61K 36/00* (2006.01)

(52) U.S. Cl.
USPC .......................... 424/728; 424/725

(58) Field of Classification Search
USPC .................. 424/728, 725
See application file for complete search history.

(56) References Cited

U.S. PATENT DOCUMENTS

| | | | | |
|---|---|---|---|---|
| 2003/0175315 A1* | 9/2003 | Yoo et al. | ........................ | 424/400 |
| 2003/0190378 A1* | 10/2003 | Kim et al. | ........................ | 424/728 |
| 2010/0310485 A1* | 12/2010 | Park et al. | ........................ | 424/62 |

FOREIGN PATENT DOCUMENTS

| | | |
|---|---|---|
| CN | 1417345 A | 5/2003 |
| CN | 1899366 A | 1/2007 |
| JP | 2004-49154 | 2/2004 |
| KR | 1987-0000031 | 2/1987 |
| KR | 10-1998-0066516 A | 10/1998 |
| KR | 10-2002-0009756 A | 2/2002 |
| KR | 2002-0040533 | 5/2002 |
| KR | 10-0377546 | 3/2003 |
| KR | 10-2003-0037005 A | 5/2003 |
| KR | 2003037005 A * | 5/2003 |
| KR | 2003-0094757 | 12/2003 |
| KR | 10-0418604 | 2/2004 |
| KR | 2005077140 A * | 8/2005 |
| KR | 20040005048 * | 8/2005 |
| WO | WO 2004/095949 | 11/2004 |

OTHER PUBLICATIONS

U.S. Appl. No. 12/857,707, filed Aug. 17, 2010, Konn, et al.
Jia-Yan Wu, et al., "Saponin Adjuvant Enhancement of Antigen-Specific Immune Responses to an Experimental HIV-1 Vaccine", The Journal of Immunology, vol. 148, No. 5, Mar. 1, 1992, pp. 1519-1525.
Katsuaki Sato, et al., "Inhibition of Tumor Angiogenesis and Metastasis by a Saponin of Panax ginseng, Ginsenoside-Rb2", Biol. Pharm. Bull. 17 (5), May 1994, pp. 635-639.
Mami Mochizuki, et al., "Inhibitory Effect of Tumor Metastasis in Mice by Saponins, Ginsenoside-Rb2, 20(R)- and 20(S)-Ginsenoside-Rg3, of Red ginseng", Biol. Pharm. Bull., vol. 18, No. 9, Sep. 1995, pp. 1197-1202.

(Continued)

*Primary Examiner* — Patricia Leith
(74) *Attorney, Agent, or Firm* — Oblon, Spivak, McClelland, Maier & Neustadt, L.L.P.

(57) ABSTRACT

The present invention relates to a method for preparing a fermented ginseng concentrate. The method first involves subjecting ginseng to an extraction with a solvent to obtain a ginseng extract. Next, pectinase and beta-galactosidase are added to the ginseng extract under conditions effective to ferment the ginseng extract. The fermented extract is then concentrated to produce a fermented ginseng concentrate. The method may further involve drying the fermented ginseng concentrate to obtain fermented ginseng powder.

10 Claims, 3 Drawing Sheets

Analysis of Each Individual (C max)

Ginseng concentrate
IH-901(Cmax)

Fermented Ginseng Concentrate
IH-901(Cmax)

(56) References Cited

OTHER PUBLICATIONS

Masami Karikura, et al., "Studies on Absorption, Distribution, Excretion and Metabolism of Ginseng Saponins. VII.[1] Comparison of the Decomposition Modes of Ginsenoside-$Rb_1$ and -$Rb_2$ in the Digestive Tract of Rats", Chem. Pharm. Bull., vol. 39, No. 9, Sep. 1991, pp. 2357-2361.

Matao Kanaoka, et al., "Metabolism of Ginseng Saponins, Ginsenosides, by Human Intestinal Flora", Journal of Traditional Medicinen, vol. 11, No. 3, 1994, pp. 241-245 (with English Abstract and English translation).

Teruaki Akao, et al., "Appearance of Compound K, a Major Metabolite of Ginsenoside $Rb_1$ by Intestinal Bacteria, in Rat Plasma after Oral Administration—Measurement of Compound K by Enzyme Immunoassay—", Biol. Pharm. Bull., vol. 21, No. 3. Mar. 1998, pp. 245-249.

Hideo Hasegawa, et al., "Role of Human Intestinal Prevotella oris in Hydrolyzing Ginseng Saponins", Planta Medica, 63, 1997, pp. 436-440.

Mona Abdel Tawab, et al., "Degradation of Ginsenosides in Humans After Oral Administration", Drug Metabolism and Disposition, vol. 31, No. 8, 2003, pp. 1065-1071.

Yun Suk Choi, et al., "Effects of Compound K on Insulin Secretion and Carbohydrate Metabolism", J. Ginseng Res., vol. 31, No. 2, 2007, pp. 79-85 (with English Abstract and English translation).

Chisato Wakabayashi, et al., "In Vivo Antimetastatic Action of Ginseng Protopanaxadiol Saponins Is Based on Their Intestinal Bacterial Metabolites After Oral Administration", Oncology Research, vol. 9, 1997, pp. 411-417.

Sang-Jun Lee, et al., "Antitumor Activity of a Novel Ginseng Saponin Metabolite in Human Pulmonary Adenocarcinoma Cells Resistant to Cisplatin", Cancer Letters, 144, 1999, pp. 39-43.

B.H. Han, et al., "Degradation of Ginseng Saponins Under Mild Acidic Conditions", Planta Medica, vol. 44, 1982, pp. 146-149.

Yingjie Chen, et al., "Alkaline Cleavage of Ginsenosides", Chem. Pharm. Bull., vol. 35, No. 4, 1987, pp. 1653-1655.

G. B. Elyakov, et al., "Synthesis of the Ginseng Glycosides and Their Analogs", Proc. 6th Int. Ginseng Symp., 1993, pp. 74-83.

Sung-Ryong Ko, et al., "Enzymatic Preparation of Genuine Prosapogenin, 20(S)-Ginsenoside $Rh_1$, from Ginsenosides Re and $Rg_1$", Biosci. Biotechnol. Biochem., 64 (12), 2000, pp. 2739-2743.

Sung-Ryong Ko, et al., "Enzymatic Preparation of Ginsenosides $Rg_2$, $Rh_1$, and $F_1$ from Protopanaxatriol-Type Ginseng Saponin Mixture", Planta Med., 69, 2003, pp. 285-286.

Eun-Ah Bae, et al., "Transformation of Ginsenosides to Compound K (IH-901) by Lactic Acid Bacteria of Human Intestine", J. Microbiol. Biotechnol., 13 (1), 2003, pp. 9-14.

Masami Karikura, et al., "Studies on Absorption, Distribution, Excretion and Metabolism of Ginseng Saponins. V.[1] The Decompostion Products of Ginsenoside $Rb_2$ in the Large Intestine of Rats", Chem. Pharm. Bull., vol. 38. No. 10, Oct. 1990, pp. 2859-2861.

Lee, "What Ginseng Does", Facts about Ginseng, the Elixir of Life, Hollyn International, Chapter 6, 1992, pp. 41-59.

Huang, "Herbs with Multiple Actions", The Pharmacology of Chinese Herbs, CRC Press, 1999, pp. 17-44.

Chang, "Pharmacology and Application of Chinese Material Medica", World Scientific, vol. 1, 1986, pp. 1-724 (entire book).

Office Action issued Apr. 22, 2013, in Chinese Patent Application No. 200980160042.9 (with English-language Translation).

Sung-Ryong Ko, et al., "Marked Production of Ginsenosides Rd, $F_2$, $Rg_3$, and Compound K by Enzymatic Method," *Chem. Pharm. Bull.* 55 (10) 1522-1527 (2007).

Bo-Hye Kim, et al., "Biotransformation of Korean Panax Ginseng by Pectinex," *Biol. Pharm. Bull.*, 29 (12) 2472-2478 (2006).

\* cited by examiner

Auto-scaled Chromatogram

Average Blood Concentration of IH-901 Over Time

Analysis of Each Individual (C max)

Analysis of Each Individual (T max)

METHODS FOR PREPARING A FERMENTED GINSENG CONCENTRATE OR POWDER

TECHNICAL FIELD

The present invention relates to methods for preparing a fermented ginseng concentrate or powder.

BACKGROUND OF THE INVENTION

*Panax ginseng* C. A. Meyer (Araliaceae), is one of the medicinal plants that have long been used for treating various diseases in Asian countries, including China, Korea, and Japan. In particular, ginsenosides (ginseng saponin), the main active ingredient of *Panax ginseng*, are known to have various physiological activities, such as anti-aging activity, anti-inflammatory activity, antioxidant activities in the central nervous system, cardiovascular system, and the immune system (Wu et al., *J. Immunol.*, 148:1519-25, 1992; Lee, *Facts about Ginseng, the Elixir of Life.*, Hollyn International. New Jersey, 1992; Huang, *The Pharmacology of Chinese Herbs.* CRC Press. Florida, 1999), anti-diabetic activity (Chang, *Pharmacology and Application of Chinese Material Medica*. Vol. 1, World Scientific. Singapore, 1986), and anti-tumor activity (Sato et al., *Biol. Pharm. Bull.* 17:635-9, 1994; Mochizuki et al., *Biol. Pharm. Bull.* 18:1197-1202, 1995).

Further, ginsenosides are metabolized by bacteria inside the human intestine after intake, where their metabolites are known to have various physiological activities (Karikura et al., *Chem. Pharm. Bull.*, 39:2357-61, 1991; Kanaoda et al., *J. Tradit. Med.* 11:241-5, 1994; Akao et al., *Biol. Pharm. Bull.*, 21:245-9, 1998). For example, Rb1, Rb2, and Rc, which are protopanaxadiol-type ginsenosides, are metabolized by human intestinal bacteria into IH-901 (20-O-$\beta$-D-glucopyranosyl-20(S)-protopandaxadiol) (Hasegawa et al., *Planta Medica* 63:463-40, 1997; Tawab et al., *Drug Metab. Dispos.*, 31:1065-71, 2003), while Re and Rg1, protopanaxatriol-type ginsenosides, are metabolized into ginsenoside Rh1 or ginsenoside F1 (Hasegawa et al., *Planta Medica* 63:463-40, 1997; Tawab et al., *Drug Metab. Dispos.*, 31:1065-71, 2003), where the metabolites IH-901, Rh1, and F1 exhibit various physiological activities.

Specifically, IH-901 is generally known for its anti-diabetic (Choi et al., *J Ginseng Res.* 31(2): 79-85, 2007) and immune-enhancing activities. Further, IH-901 is known to induce an anti-metastasis or anti-cancer effect by blocking tumor invasion or preventing chromosomal mutation and tumor formation (Wakabayashi et al., *Oncol. Res.*, 9:411-7, 1998; Lee et al., *Cancer Lett.*, 144:39-43, 1999).

Several researchers have tried to produce genuine prosapogenin or sapogenin by using methods, such as chemical synthesis, subacid hydrolysis, and alkali digestion (Han et al., *Planta Medica* 44:146-9, 1982; Chen et al., *Chem. Pharm. Bull.* 35:1653-5, 1987; Elyakov et al., Synthesis of the Ginseng Glycosides and Their Analogs. *Proc. 6th Int. Ginseng Symp.* Seoul 74-83, 1993). However, the above methods are known to cause various side reactions, such as epimerization, hydration, and hydroxylation.

Thus, a number of methods that convert ginsenosides under mild conditions by utilizing enzymes (Ko et al., *Biosci. Biotechnol. Biochem.* 64:2739-43, 2000; Ko et al., *Planta Med.* 69:285-6, 2003) or intestinal bacteria (Hasegawa et al., *Planta Medica* 63:463-40, 1997; Bae et al., *J. Microbial. Biotechnol.* 13:9-14, 2003) have been studied. Specifically, methods for preparing IH-901 by hydrolyzing diol-type ginsenosides with naringinase, as well as methods for preparing IH-901 by administrating the diol-type ginsenosides orally to a rat and then having them digested in the colon have been developed. However, the above preparation methods were found to have certain drawbacks in that the production yield of IH-901 is extremely low and various secondary metabolites are produced, making it difficult to obtain highly pure IH-901 (Karikura et al., *Chem. Pharm. Bull.* 38:2859, 1990).

More recently, other methods for preparing IH-901 by reacting a variety of enzymes with ginsenosides (Korean Laid-open Patent Publication No. 2003-94757; Korean Patent Nos. 418604 and 377546) have been studied, but the amount of IH-901 produced using these methods was found to be too low to have any significant effect. Further, the above methods involve complicated steps and are unsuitable for preparing a fermented ginseng concentrate having a high content of IH-901.

The present invention is directed to overcoming these deficiencies in the art.

SUMMARY OF THE INVENTION

The present invention relates to a method for preparing a fermented ginseng concentrate. The method first involves subjecting ginseng to an extraction with a solvent to obtain a ginseng extract. Next, pectinase and beta-galactosidase are added to the ginseng extract under conditions effective to ferment the ginseng extract. Then, the fermented ginseng extract is concentrated to produce a fermented ginseng concentrate.

The present invention also relates to a method for preparing a fermented ginseng concentrate. The method first involves suspending ginseng in a first solvent to obtain a ginseng solution. Next, pectinase and beta-galactosidase are added to the ginseng solution under conditions effective to ferment the ginseng solution. Then, the fermented ginseng solution is subjected to an extraction with a second solvent to obtain a fermented ginseng extract. Finally, the fermented ginseng extract is concentrated to produce a fermented ginseng concentrate.

Another aspect of the present invention relates to fermented ginseng concentrates and fermented ginseng powder prepared by the above methods, as well as food compositions or functional food compositions containing such fermented ginseng concentrates and powder.

The methods for preparing a fermented ginseng concentrate and fermented ginseng powder according to the present invention involve simple steps and are capable of producing a fermented ginseng concentrate or powder having a high IH-901 content. Due to their high IH-901 content, the fermented ginseng concentrate or powder prepared according to the methods of the present invention can be effectively used in functional food compositions.

DETAILED DESCRIPTION OF THE INVENTION

Figure 1:
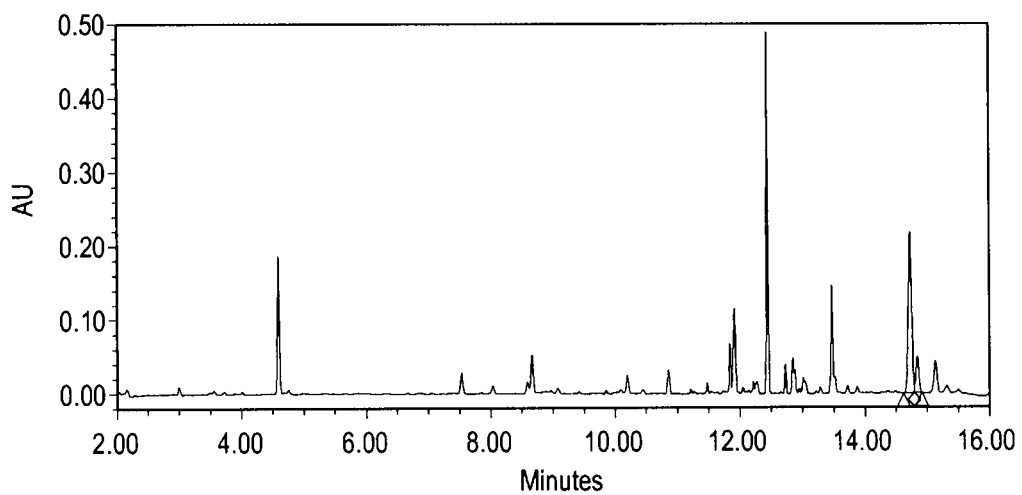
FIG. 1 is a graph depicting the results from a high-pressure liquid chromatography analysis of the fermented ginseng concentrate of the present invention.

The present invention relates to a method for preparing a fermented ginseng concentrate.

The method first involves subjecting ginseng to an extraction with a solvent to obtain a ginseng extract. Examples of ginseng may include, but are not limited to, ginseng tail, white ginseng, fresh ginseng, dried ginseng, red ginseng, taekuk ginseng, Korean ginseng, Chinese ginseng, Japanese ginseng, Asian ginseng, American ginseng, extracts thereof, powders thereof, and mixtures thereof.

The solvent used in the extraction of ginseng may be any solvent, such as an aqueous solvent (e.g., water), an organic solvent, or any mixture thereof, as long as it does not affect the activity of the enzymes used in the method. In some embodiments, the organic solvent may include, without limitation, acetonitrile, dioxane, dimethyl sulfoxide, methanol, ethanol, 1-propanol, 2-propanol, and mixtures thereof.

In some embodiments, the ginseng may be subjected to an extraction with the above solvents by using any commonly known solvent extraction methods. In certain embodiments, an appropriate mixture of water and organic solvents may be used for the extraction, where the organic solvent in the mixture may increase the solubility of the ingredients in ginseng that are insoluble in water and/or the intermediates produced from the enzymatic reactions, resulting in an overall increase in the IH-901 content in the final product, i.e., the fermented ginseng concentrate or powder.

Next, pectinase and beta-galactosidase are added to the ginseng extract under conditions effective to ferment the ginseng extract. In some embodiments, the ginseng extract may be diluted with a solvent before the pectinase and the beta-galactosidase are added. In some embodiments, the pectinase and the beta-galactosidase are added to the ginseng extract together or at the same time. In other embodiments, the pectinase and the beta-galactosidase are added to the ginseng extract separately or at different times.

In some embodiments, the pectinase and the beta-galactosidase may be added to the ginseng extract in a relative ratio ranging from about 100:1 to about 1:100, from about 50:1 to about 1:50, from about 20:1 to about 1:20, from about 10:1 to about 1:10, from about 5:1 to about 1:5, from about 3:1 to about 1:3, or from about 2:1 to about 1:2. In other embodiments, the pectinase and the beta-galactosidase may be added to the ginseng extract in a relative ratio of about 100:1, about 50:1, about 20:1, about 10:1, about 5:1, about 3:1, about 2:1, about 1:2, about 1:3, about 1:5, about 1:10, about 1:20, about 1:50, or about 1:100.

In some embodiments, the total amount of the pectinase and beta-galactosidase added to the ginseng extract may range from about 0.01 wt. % to about 50 wt. %, from about 0.05 wt. % to about 50 wt. %, from about 0.1 wt. % to about 50 wt. %, from about 0.5 wt. % to about 50 wt. %, from about 1 wt. % to about 50 wt. %, from about 2 wt. % to about 50 wt. %, from about 5 wt. % to about 50 wt. %, from about 10 wt. % to about 50 wt. %, from about 25 wt. % to about 50 wt. %, from about 0.01 wt. % to about 0.05 wt. %, from about 0.01 wt. % to about 0.1 wt. %, from about 0.01 wt. % to about 0.5 wt. %, from about 0.01 wt. % to about 1 wt. %, from about 0.01 wt. % to about 2 wt. %, from about 0.01 wt. % to about 5 wt. %, from about 0.01 wt. % to about 10 wt. %, from about 0.01 wt. % to about 25 wt. %, from about 0.05 wt. % to about 0.1 wt. %, from about 0.1 wt. % to about 0.5 wt. %, from about 0.5 wt. % to about 1 wt. %, from about 1 wt. % to about 2 wt. %, from about 2 wt. % to about 5 wt. %, from about 5 wt. % to about 10 wt. %, or from about 10 wt. % to about 25 wt. %, based on the total weight of the ginseng extract or ginseng. In other embodiments, the total amount of the pectinase and beta-galactosidase added to the ginseng extract may be about 0.01 wt. %, about 0.05 wt. %, about 0.1 wt. %, about 0.5 wt. %, about 1 wt. %, about 2 wt. %, about 5 wt. %, about 10 wt. %, about 25 wt. %, or about 50 wt. %, based on the total weight of the ginseng extract or ginseng.

In some embodiments, the pectinase and the beta-galactosidase are added to the ginseng extract where the reaction is carried out at a pH of from about 3 to about 8, from about 4 to about 8, from about 4.5 to about 8, from about 5 to about 8, from about 6 to about 8, from about 3 to about 4, from about 3 to about 4.5, from about 3 to about 5, from about 3 to about 6, from about 4 to about 4.5, from about 4.5 to about 5, or from about 5 to about 6. In other embodiments, the reaction is carried out at a pH of about 3, about 4, about 4.5, about 5, about 6, or about 8. The reaction, however, may be carried out at any pH as long as the activities of the pectinase and the beta-galactosidase are maintained. The pH may be adjusted by adding to the ginseng extract solutions, such as but not limited to, a phosphate solution, citric acid solution, and sodium citrate buffer solution.

The reaction temperature for adding the pectinase and the beta-galactosidase to the ginseng extract may be any temperature as long as the activities of the pectinase and beta-galactosidase are maintained. In some embodiments, the reaction temperature range may range from about 10° C. to about 70° C., from about 30° C. to about 70° C., from about 40° C. to about 70° C., from about 50° C. to about 70° C., from about 60° C. to about 70° C., from about 10° C. to about 30° C., from about 10° C. to about 40° C., from about 10° C. to about 50° C., from about 10° C. to about 60° C., from about 30° C. to about 40° C., from about 40° C. to about 50° C., or from about 50° C. to about 60° C. In other embodiments, the reaction temperature may be about 10° C., about 30° C., about 40° C., about 50° C., about 60° C., or about 70° C.

Further, the reaction time may be any length of time, as long as the activities of the pectinase and beta-galactosidase are maintained. In some embodiments, the reaction time may range from about 1 hour to about 72 hours, from about 12 hours to about 72 hours, from about 24 hours to about 72 hours, from about 48 hours to about 72 hours, from about 60 hours to about 72 hours, from about 1 hour to about 12 hours, from about 1 hour to about 24 hours, from about 1 hour to about 48 hours, from about 1 hour to about 60 hours, from about 12 hours to about 24 hours, from about 24 to about 48 hours, or from about 48 to about 60 hours. In other embodiments, the reaction time may be about 1 hour, about 12 hours, about 24 hours, about 48 hours, about 60 hours, or about 72 hours.

Finally, the fermented ginseng extract is concentrated to produce a fermented ginseng concentrate. In some embodiments, the concentrating of the fermented ginseng extract may involve initially carrying out a centrifugation of the fermented ginseng extract and then concentrating only the separated supernatant. In other embodiments, the concentrating of the fermented ginseng extract may involve concentrating the fermented ginseng extract without any pre-processing steps. The fermented ginseng extract may be concentrated by using commonly used devices, such as but not limited to, a vacuum decompression concentrator.

In some embodiments, the method of the present invention may further include drying the prepared fermented ginseng concentrate (which may be in a liquid form) to produce fermented ginseng powder. The drying may be carried out by any conventional drying method, such as but not limited to, drying under reduced pressure, hot-air drying, spray drying, fluidized bed drying, fluidized bed granulation, and freeze drying or lyophilization.

The present invention also relates to a method for preparing a fermented ginseng concentrate. The method first involves suspending ginseng in a first solvent to obtain a ginseng solution. Next, pectinase and beta-galactosidase are added to the ginseng solution under conditions effective to ferment the ginseng solution. Then, the fermented ginseng solution is subjected to an extraction with a second solvent to obtain a fermented ginseng extract. In some embodiments, the first and second solvents may be an aqueous solvent (e.g., water), an organic solvent, or a mixture thereof. Finally, the fermented ginseng extract is concentrated to produce a fermented ginseng concentrate. Descriptions regarding the various conditions used in this method, for example, with respect to addition of the pectinase and beta-galactosidase, extraction, and concentration already described above are not necessarily repeated herein.

Another aspect of the present invention relates to fermented ginseng concentrates and fermented ginseng powder prepared by the above methods. The above methods of the present invention involve directly adding pectinase and beta-galactosidase to a ginseng extract or ginseng solution under conditions effective to ferment the ginseng extract or solution and thus are simple methods for preparing fermented ginseng concentrates or powder having a high IH-901 content. Since the fermented ginseng concentrate and powder prepared by the above methods of the present invention have a high IH-901 content, they can be effectively used as functional food compositions.

Another aspect of the present invention relates to food compositions containing the above fermented ginseng concentrate or powder, as well as functional food compositions containing a therapeutically effective amount of the above fermented ginseng concentrate or powder.

The fermented ginseng concentrate and powder of the present invention may contain a large amount of IH-901, which is known to possess immune-enhancing, anti-diabetic, anticancer, anti-aging, and anti-oxidation activities. A person skilled in the art can properly determine the amount of the fermented ginseng concentrate or powder of the present invention to be added, depending on the purpose for using the functional food composition. Generally, the fermented ginseng concentrate or powder of the present invention may be added to the functional food composition in an amount ranging from about 0.1 wt % to about 100 wt %, based on the total weight of the functional food composition. In certain embodiments, such as when taking the functional food composition on a long term basis for health management, the amount of the fermented ginseng concentrate or powder of the present invention added to the functional food composition may be lower than the above range. Since there are no safety issues, however, the fermented ginseng concentrate or powder of the present invention may be used in a very large amount.

In some embodiments, the food compositions or functional food compositions of the present invention may be prepared by adding the fermented ginseng concentrate or powder of the present invention or mixtures thereof without any pre-processing. In other embodiments, the fermented ginseng concentrate or powder of the present invention may be initially processed by commonly known methods and other food components may then be added. The food components that may be added to the food composition or functional food composition of the present invention may differ depending on the type of the food composition or functional food composition, and are not limited as long as they do not cause any side effects when mixed with the fermented ginseng concentrate or powder of the present invention.

The food compositions or functional food compositions of the present invention may be in a form suitable for oral consumption, for example, as soft or hard capsules, tablets, lozenges, dispersible powders or granules, emulsions, suspensions, and tea bags composed of dried powder made by commonly known methods. In some embodiments, the functional food composition may be added to various foods, such as but not limited to, beverages, gum, candies, snacks, vitamin complexes, health functional foods, etc., to provide immune-enhancing, anti-diabetic, anti-cancer, anti-oxidation, and/or anti-aging effects.

EXAMPLES

The following examples are provided to illustrate embodiments of the present invention but are by no means intended to limit its scope.

Example 1

Preparation of Fermented Ginseng Concentrate Using Pectinase and Beta-Galactosidase <1-1> Preparation of Fermented Ginseng Concentrate Using Ginseng Tail and White Ginseng 5 g of ginseng tail and 5 g of white ginseng were extracted with a mixture of water and ethanol (mixing ratio of 1:1; in an amount corresponding to 500% compared to the raw materials) four times at 80° C. at 3-hour intervals to obtain 7 g of ginseng extract. 100 ml of water and then 0.3 g of pectinase and 1 g of beta-galactosidase were added to the ginseng extract, where the reaction mixture was maintained at 50° C., pH 4-5, for 48 hours. The reactant was filtered and concentrated under reduced pressure at 80° C. to give 6.3 g of fermented ginseng concentrate according to the present invention.

<1-2> Preparation of Fermented Ginseng Concentrate Using Ginseng Tail and White Ginseng 7 g of ginseng extract was prepared as described in Example <1-1> above. 100 ml of water and then 1 g of beta-galactosidase were added to the ginseng extract, where the reaction mixture was maintained at 50° C. for 24 hours, and then the enzyme was inactivated by subjecting the mixture at a temperature of 80° C. for 3 hours. The reactant was cooled and the pH was adjusted to 4-5 with citric acid. Then, 0.3 g of pectinase was added thereto where the mixture was subjected to a reaction for 24 hours. Subsequently, the reaction mixture was filtered and concentrated under reduced pressure at 80° C. to give 5.9 g of fermented ginseng concentrate according to the present invention.

<1-3> Preparation of Fermented Ginseng Concentrate Using Ginseng Tail and White Ginseng 5 g of ginseng tail and 5 g of white ginseng were extracted with a mixture of water and ethanol (mixing ratio of 1:1; in an amount corresponding to 500% compared to the raw materials) to obtain 7 g of ginseng extract. 100 ml of water and then 0.5 g of pectinase and 0.7 g of beta-galactosidase were added to the ginseng extract, where the reaction mixture was maintained at 50° C., pH 4-5, for 48 hours. The reactant was filtered and concentrated under reduced pressure at 80° C. to give 6.2 g of fermented ginseng concentrate according to the present invention.

<1-4> Preparation of Fermented Ginseng Concentrate Using Ginseng Tail and White Ginseng 5 g of ginseng tail and 5 g of white ginseng were extracted with a mixture of water and ethanol (mixing ratio of 1:1; in an amount corresponding to 500% compared to the raw materials) to obtain 7 g of ginseng extract. 100 ml of water and then 0.9 g of pectinase and 0.6 g of beta-galactosidase were added to the ginseng extract, where the reaction mixture was maintained at 50° C., pH 4-5, for 48 hours. The reactant was filtered and concentrated under reduced pressure at 80° C. to give 5.9 g of fermented ginseng concentrate according to the present invention.

<1-5> Preparation of Fermented Ginseng Concentrate Using Ginseng Tail and White Ginseng 5 g of ginseng tail and 5 g of white ginseng were extracted with a mixture of water and ethanol (mixing ratio of 1:1; in an amount corresponding to 500% compared to the raw materials) to obtain 7 g of ginseng extract. 100 ml of water and then 1.2 g of pectinase and 0.2 g of beta-galactosidase were added to the ginseng extract, where the reaction mixture was maintained at 50° C., pH 4-5, for 48 hours. The reactant was filtered and concentrated under reduced pressure at 80° C. to give 6.3 g of fermented ginseng concentrate according to the present invention.

<1-6> Preparation of Fermented Ginseng Concentrate Using Ginseng Tail 10 g of ginseng tail was extracted with 100 ml of water to obtain 7 g of ginseng extract. The pH of the extract was adjusted to 3-4 with citric acid. 0.3 g of pectinase and 1 g of beta-galactosidase were added to the ginseng extract, where the mixture was subjected to a reaction at 50° C. for 48 hours. Subsequently, the reactant was filtered and concentrated by the same method as described in Example <1-1> above to obtain 6.5 g of fermented ginseng concentrate (I) according to the present invention.

Alternatively, 10 g of ginseng tail was extracted with a mixture of water and ethanol by the same method as described in Example <1-1> above to obtain 7.2 g of ginseng extract. The pH of the extract was adjusted to 3-4 with citric acid. 0.3 g of pectinase and 1 g of beta-galactosidase were added to the ginseng extract, where the mixture was filtered and concentrated by the same method as described in Example <1-1> above to obtain 6.8 g of fermented ginseng concentrate (II) according to the present invention.

<1-7> Preparation of Fermented Ginseng Concentrate Using Ginseng Tail 10 g of ginseng tail was extracted with 100 ml of water to obtain 7 g of ginseng extract. 100 ml of water and then 1 g of beta-galactosidase were added to the ginseng extract where the reaction mixture was maintained at 50° C. for 24 hours, and then the enzyme was inactivated by subjecting the mixture at a temperature of 80° C. for 3 hours. The reactant was cooled and the pH was adjusted to 4-5 with citric acid. Then, 0.3 g of pectinase was added thereto and reacted at 50° C. for 24 hours. Subsequently, the reactant was filtered and concentrated under reduced pressure at 80° C. to obtain 6.5 g of fermented ginseng concentrate according to the present invention.

<1-8> Preparation of Fermented Ginseng Concentrate Using White Ginseng 1 kg of white ginseng was extracted with 5 l of ethanol to obtain 540 g of ginseng extract. 7 g of the extract was concentrated and then suspended in water. 0.3 g of pectinase and 1 g of beta-galactosidase were added thereto, where the mixture was reacted, filtered, and concentrated by the same method as described in Example <1-1> above to obtain 5.2 g of fermented ginseng concentrate according to the present invention.

<1-9> Preparation of Fermented Ginseng Concentrate Using White Ginseng 1 kg of white ginseng was extracted with 5 l of ethanol to obtain 540 g of ginseng extract. 7 g of the extract was concentrated and then suspended in water. 0.5 g of pectinase and 0.5 g of beta-galactosidase were added thereto, where the mixture was reacted, filtered, and concentrated by the same method as described in Example <1-1> above to obtain 5.1 g of fermented ginseng concentrate according to the present invention.

<1-10> Preparation of Fermented Ginseng Concentrate Using White Ginseng 1 kg of white ginseng was extracted with 5 l of ethanol to obtain 540 g of ginseng extract. 7 g of the extract was concentrated and then suspended in water. 1.5 g of pectinase and 0.2 g of beta-galactosidase were added thereto, where the mixture was reacted, filtered, and concentrated by the same method as described in Example <1-1> above to obtain 6.2 g of fermented ginseng concentrate according to the present invention.

<1-11> Preparation of Fermented Ginseng Concentrate Using Fresh Ginseng 6 g of fresh ginseng was sliced into pieces and sterilized. After the ginseng pieces were suspended in water, the pH was adjusted to 3-4.5 with citric acid, and 0.3 g of pectinase and 1 g of beta-galactosidase were added thereto where the mixture was subjected to a reaction at 50° C. for 72 hours. The reactant was extracted with a mixture of water and ethanol prepared by the same method as described in Example <1-1> above four times at 80° C. for 4 hours. Then, the extract was filtered and concentrated to obtain 3.5 g of fermented ginseng concentrate according to the present invention.

<1-12> Preparation of Fermented Ginseng Concentrate Using Fresh Ginseng 6 g of fresh ginseng was sliced into pieces and sterilized. After the ginseng pieces were suspended in water, 1 g of beta-galactosidase was added thereto where the mixture was subjected to a reaction at 50° C. for 24 hours and inactivated at 80° C. for 3 hours. The reactant was cooled and the pH was adjusted to 4-5 with citric acid. Then, 0.3 g of pectinase was added thereto and reacted at 50° C. for 24 hours. Subsequently, the reactant was filtered and then extracted with a mixture of water and ethanol prepared by the same method as described in Example <1-1> above four times at 80° C. for 4 hours. Then, the extract was concentrated under reduced pressure at 80° C. to obtain 2.9 g of fermented ginseng concentrate according to the present invention.

<1-13> Preparation of Fermented Ginseng Concentrate Using Fresh Ginseng 6 g of fresh ginseng was sliced into pieces and sterilized. After the ginseng pieces were suspended in water, the pH was adjusted to 3-4 with citric acid. Then, 0.7 g of pectinase and 0.6 g of beta-galactosidase were added thereto where the mixture was subjected to a reaction at 50° C. for 72 hours. Subsequently, the reactant was filtered and concentrated to obtain 2.9 g of fermented ginseng concentrate according to the present invention.

<1-14> Preparation of Fermented Ginseng Concentrate Using Fresh Ginseng 6 g of fresh ginseng was sliced into pieces and sterilized. After the ginseng pieces were suspended in water, 0.7 g of beta-galactosidase was added thereto where the mixture was subjected to a reaction at 50° C. for 24 hours and inactivated at 80° C. for 3 hours. The reactant was cooled and the pH was adjusted to 4-5 with citric acid. Then, 0.6 g of pectinase was added thereto and reacted at 50° C. for 24 hours. Subsequently, the reactant was filtered and then extracted with a mixture of water and ethanol prepared by the same method as described in Example <1-1> above four times at 80° C. for 4 hours. Then, the extract was concentrated under reduced pressure at 80° C. to obtain 2.3 g of fermented ginseng concentrate according to the present invention.

<1-15> Preparation of Fermented Ginseng Concentrate Using Fresh Ginseng 6 g of fresh ginseng was sliced into pieces and sterilized. After the ginseng pieces were suspended in water, the pH was adjusted to 3-4.5 with citric acid. Then, 0.9 g of pectinase and 0.5 g of beta-galactosidase were added thereto where the mixture was subjected to a reaction at 50° C. for 72 hours. Subsequently, the reactant was filtered and concentrated to obtain 2.5 g of fermented ginseng concentrate according to the present invention.

<1-16> Preparation of Fermented Ginseng Concentrate Using Fresh Ginseng 6 g of fresh ginseng was sliced into pieces and sterilized. After the ginseng pieces were suspended in water, the pH was adjusted to 3-4.5 with citric acid. Then, 2 g of pectinase and 0.2 g of beta-galactosidase were added thereto where the mixture was subjected to a reaction at 50° C. for 72 hours. Subsequently, the reactant was filtered and concentrated to obtain 3.3 g of fermented ginseng concentrate according to the present invention.

<1-17> Preparation of Fermented Ginseng Concentrate Using Fresh Ginseng 6 g of fresh ginseng was sliced into pieces and sterilized. After the ginseng pieces were suspended in water, 0.5 g of beta-galactosidase was added thereto where the mixture was subjected to a reaction at 50° C. for 24 hours and inactivated at 80° C. for 3 hours. The reactant was cooled and the pH was adjusted to 4-5 with citric acid. Then, 1.5 g of pectinase was added thereto and reacted at 50° C. for 24 hours. Subsequently, the reactant was filtered and then extracted with a mixture of water and ethanol prepared by the same method as described in Example <1-1> above four times at 80° C. for 4 hours. Then, the extract was concentrated under reduced pressure at 80° C. to obtain 3.1 g of fermented ginseng concentrate according to the present invention.

<1-18> Preparation of Fermented Ginseng Concentrate Using Ginseng Powder 7 g of ginseng powder was suspended in water. The pH was adjusted to 3-4.5 with citric acid. The suspended ginseng powder was reacted with 0.3 g of pectinase and 1 g of beta-galactosidase and extracted by the same method as described in Example <1-11> above, and then filtered and concentrated to obtain 3.7 g of fermented ginseng concentrate according to the present invention.

Comparative Example 1

Preparation of Fermented Ginseng Concentrate Using Pectinase Only 100 ml of water was added to 7 g of ginseng extract prepared by the same method as described in Example <1-1> above. Then, 1.3 g of pectinase was added to the extract, which was subsequently reacted and concentrated under reduced pressure by the same method as described in Example <1-1> above to obtain 5.6 g of fermented ginseng concentrate according to the present invention.

Comparative Example 2

Preparation of Fermented Ginseng Concentrate Using beta-Galactosidase Only 100 ml of water was added to 7 g of ginseng extract prepared by the same method as described in Example <1-1> above. Then, 1.3 g of beta-galactosidase was added to the extract, which was subsequently reacted and concentrated under reduced pressure by the same method as described in Example <1-1> above to obtain 5.4 g of fermented ginseng concentrate according to the present invention.

Experimental Example 1

The IH-901 Content in the Fermented Ginseng Concentrate of the Present Invention In order to analyze the content of IH-901 (20-0-β-D-glucopyranosyl-20(S)-protopanaxadiol) in the fermented ginseng concentrate prepared by the method described in Example <1-1> above, 1 g of the obtained fermented ginseng concentrate was taken and extracted with 60 ml of water-saturated butanol four times. The butanol fraction was concentrated to obtain 120 mg of concentrate, and the concentrate was dissolved in methanol to analyze the IH-901 content by ultra performance liquid chromatography (HPLC). The results of the HPLC analysis are shown in FIG. 1. The IH-901 content in the ginseng extract prepared in Example <1-1> above was also measured in the same manner as above.

Further, the IH-901 content in the fermented ginseng concentrate prepared by the method described in Comparative Example 1 or Comparative Example 2 above was analyzed in the same manner as above.

The results of the above analyses are summarized in Table 1 below.

TABLE 1

| | Content of each component | | | |
|---|---|---|---|---|
| Component | Ginseng Extract of Example 1-1 | Fermented Ginseng Concentrate of Example 1-1 | Fermented Ginseng Concentrate of Comp. Example 1 | Fermented Ginseng Concentrate of Comp. Example 2 |
| Ginsenoside Rb1 | 17.6 mg/g | 1.2 mg/g | 6.3 mg/g | 3.2 mg/g |
| Ginsenoside Rb2 | 14.6 mg/g | 1.1 mg/g | 7.1 mg/g | 5.7 mg/g |
| Ginsenoside Rc | 18.9 mg/g | 0.1 mg/g | 9.3 mg/g | 6.3 mg/g |
| Ginsenoside Rd | 7.9 mg/g | 1.4 mg/g | 2.2 mg/g | 4.2 mg/g |
| IH-901 | 0 mg/g | 36 mg/g | 24 mg/g | 10 mg/g |

As shown in Table 1 above, the fermented ginseng concentrate according to the present invention, in contrast to the ginseng extract, contains a large amount of IH-901. Furthermore, the IH-901 content in the fermented ginseng concentrate according to the present invention is 3.6 times higher than that in the fermented ginseng concentrate prepared using beta-galactosidase only and 1.5 times higher than that in the fermented ginseng concentrate prepared using pectinase only.

Experimental Example 2

Study on Body's Absorption of IH-901 of the Fermented Ginseng Concentrate of the Present Invention Twenty four healthy male volunteers of ages ranging from 20 to 45, whose body weights are within 20% of the ideal body weights, were used as subjects for the study (randomized, 2×2 cross-over design).

Figure 2:
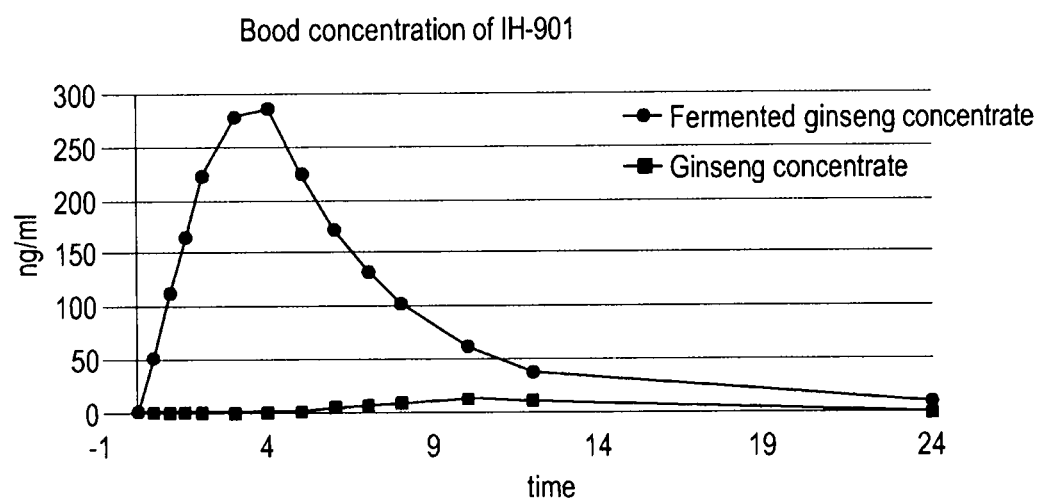
FIG. 2 is a graph showing the average plasma concentrations of IH-901 over time for the subjects who took the fermented ginseng concentrate of the present invention.
Figures 3, 4:
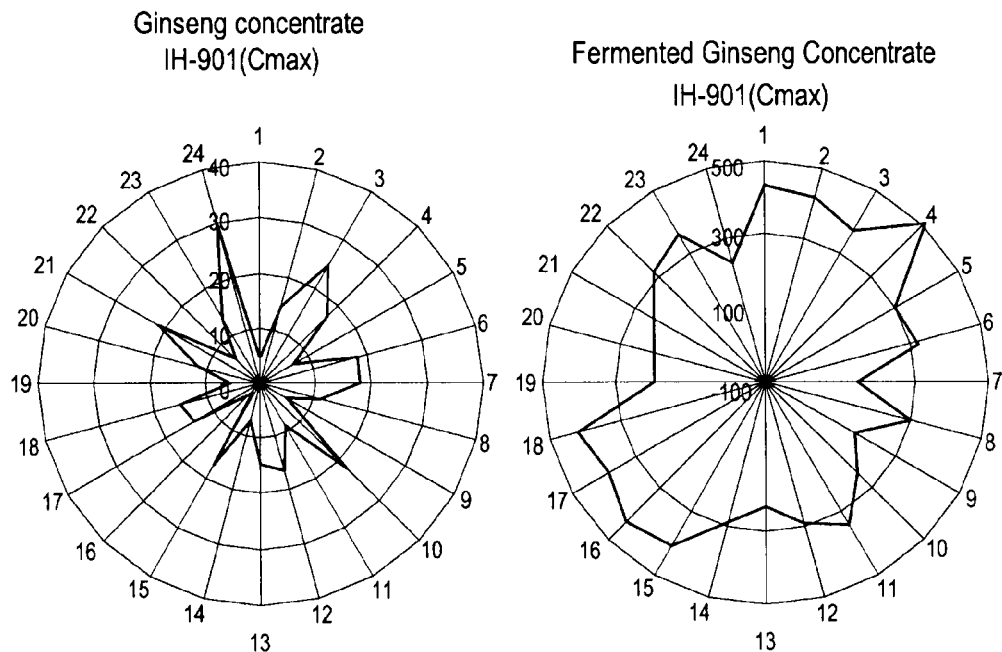
FIG. 3 is a graph showing the maximum plasma concentrations ($C_{max}$) of IH-901 of each subject.
FIG. 4 is a graph showing the times to reach maximum plasma concentration ($T_{max}$) of IH-901 of each subject.
Figure 5:
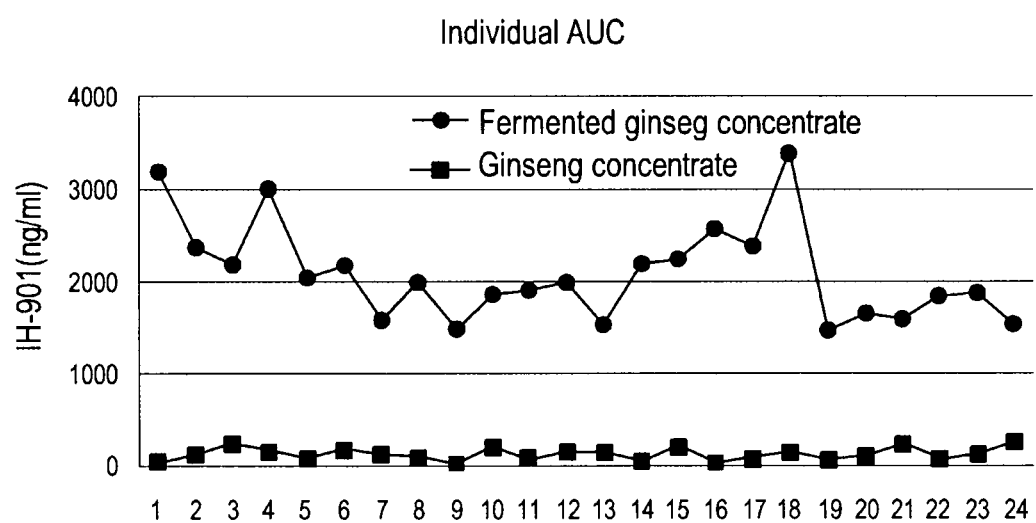
FIG. 5 is a graph showing the area under the plasma concentration time curve (AUC) of each subject.

Each volunteer received the fermented ginseng extract or ginseng extract for pharmacokinetic characteristic assessments. Blood samples were taken at 0, 0.5, 1, 1.5, 2, 3, 4, 5, 6, 7, 8, 10, 12, and 24 hours after administration of the fermented ginseng extract or ginseng extract and were analyzed by LC-MS/MS. The average plasma concentrations of IH-901 over time are shown in FIG. 2. The average maximum plasma concentration ($C_{max}$), average time to reach maximum plasma concentration ($T_{max}$), and area under the plasma concentration time curve (AUC) values measured are shown in Table 2 below, where $C_{max}$ is the average of the maximum concentration values of each subject irrespective of time and $T_{max}$ is the average of the time values corresponding to the $C_{max}$ values of each subject. The $C_{max}$, $T_{max}$, and AUC values for each subject are shown in FIGS. 3 to 5.

TABLE 2

|  | $C_{max}$ | $T_{max}$ | AUC |
|---|---|---|---|
| Fermented ginseng concentrate | 325.00 ± 91.97 ng/ml | 3.29 hr | 2083.09 ± 524.68 ng/ml |
| Ginseng concentrate | 13.88 ± 7.24 ng/ml | 12.04 hr | 134.5 ± 63.10 ng/ml |

As shown in Table 2 above, the $C_{max}$, AUC, and $T_{max}$ of IH-901 in the fermented ginseng concentrate are about 24 times higher, 15 times higher, and 3.7 times lower than those of the ginseng concentrate, respectively.

Therefore, it was found that when a ginseng concentrate was taken, each individual had different capabilities with respect to metabolizing ginsenosides to IH-901 and only a small amount of IH-901 was absorbed in the body. Further, when a ginseng concentrate was taken, each individual exhibited different average times in reaching the maximum plasma concentration.

In contrast, when a fermented ginseng concentrate was taken, the amount of IH-901 absorbed and the average time to reach maximum plasma level were constant for each individual. Further, when a fermented ginseng concentrate was taken, a large amount of IH-901 was absorbed in the body.

Accordingly, the above results demonstrate that a steady and constant effect (with little individual variation) can be expected when subjects take fermented ginseng concentrate.

Example 2

Preparation of Fermented Ginseng Powder According to the Present Invention

<2-1> Preparation of Fermented Ginseng Powder Using Ginseng Tail and White Ginseng 100 g of water was added to 7 g of an extract of ginseng prepared by the same method as described in Example <1-1> above. Then, 0.3 g of pectinase and 1 g of beta-galactosidase were added to the extract, which was subsequently reacted at 50° C., pH 4-5, for 24 hours. The reacted extract was dried under reduced pressure at 80° C. to obtain 4.23 g of fermented ginseng powder according to the present invention.

<2-2> Preparation of Fermented Ginseng Powder Using Ginseng Powder 7 g of ginseng powder was suspended in water, and then the pH was adjusted to 3-4.5. Next, 0.3 g of pectinase and 1 g of beta-galactosidase were added to the suspension, which was subsequently reacted at 50° C. for 24 hours and extracted with a mixture of water and ethanol prepared by the same method as in described in Example <1-1> above four times at 80° C. for 4 hours. The extract was then dried under reduced pressure to obtain 2.6 g of fermented ginseng powder.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for preparing a fermented ginseng concentrate having an IH-901 content of 36 mg/g based on the total amount of concentrate, comprising:
   subjecting ginseng to an extraction with a solvent selected from the group consisting of water, ethanol, and mixtures thereof, to obtain a ginseng extract;
   adding pectinase and beta-galactosidase to the ginseng extract and reacting at a pH of 3-8, a temperature of 40-70° C., and for a time of from 12 to 72 hours to ferment the ginseng extract; and
   concentrating the fermented ginseng extract to the extent necessary to produce a fermented ginseng concentrate having an IH-901 content of 36 mg/g based on the total amount of concentrate.

2. The method according to claim 1, wherein the ginseng is one or more of ginseng tail, white ginseng, fresh ginseng, dried ginseng, red ginseng, taekuk ginseng, Korean ginseng, Chinese ginseng, Japanese ginseng, Asian ginseng, American ginseng, powders thereof, and mixtures thereof.

3. The method according to claim 1, wherein said adding comprises adding the pectinase and the beta-galactosidase together.

4. The method according to claim 1, wherein said adding comprises adding the pectinase and the beta-galactosidase separately.

5. The method according to claim 1, wherein said adding comprises adding the pectinase and the beta-galactosidase in a ratio ranging from about 100:1 to about 1:100, wherein the amount of the pectinase and beta-galactosidase ranges from about 0.01 wt % to about 50 wt % based on the total amount of the ginseng extract.

6. The method according to claim 1, wherein said adding comprises adding the pectinase and the beta-galactosidase to the ginseng extract at a temperature of from about 50° C. to about 70° C.

7. The method according to claim 1, wherein said reacting occurs for a time period of about 24 hours.

8. The method according to claim 1 further comprising:
   drying the fermented ginseng concentrate after said concentrating to produce fermented ginseng powder.

9. The method according to claim 8, wherein said drying is carried out by drying under reduced pressure, hot-air drying, spray drying, fluidized bed drying, fluidized bed granulation, or freeze drying.

10. The method according to claim 1 wherein the ginseng is ginseng tail and white ginseng, wherein the solvent is a mixture of water and ethanol, wherein the pH is 4-5, wherein the fermented ginseng extract is filtered and wherein concentrating occurs under reduced pressure.

* * * * *